United States Patent [19]

Kiefer et al.

[11] Patent Number: 5,294,740

[45] Date of Patent: Mar. 15, 1994

[54] PREPARATION OF FORMIC ACID BY THERMAL CLEAVAGE OF QUATERNARY AMMONIUM FORMATES

[75] Inventors: Hans Kiefer, Neustadt; Leopold Hupfer, Friedelsheim; Ferdinand Lippert, Bad Durkheim, all of Fed. Rep. of Germany

[73] Assignee: BASF Aktiengesellschaft, Ludwigshafen, Fed. Rep. of Germany

[21] Appl. No.: 41,048

[22] Filed: Mar. 31, 1993

[30] Foreign Application Priority Data

Apr. 3, 1992 [DE] Fed. Rep. of Germany ....... 4211141

[51] Int. Cl.$^5$ ................... C07C 51/09; C07C 51/44
[52] U.S. Cl. ................................ 562/609; 568/877
[58] Field of Search ................ 562/609; 568/877

[56] References Cited

U.S. PATENT DOCUMENTS

| | | | |
|---|---|---|---|
| 3,414,610 | 12/1968 | Wagner et al. | 260/501.11 |
| 4,076,594 | 2/1978 | Buelow et al. | 203/15 |
| 4,218,568 | 8/1980 | Hohenschutz et al. | 562/609 |
| 4,262,140 | 4/1981 | Bott et al. | 562/609 |
| 4,326,073 | 4/1982 | Wolf et al. | 562/609 |
| 4,994,151 | 2/1991 | Berg et al. | 562/609 X |
| 5,189,216 | 2/1993 | Kiefer et al. | 562/609 X |
| 5,206,433 | 4/1993 | Hohenschutz et al. | 562/609 |

FOREIGN PATENT DOCUMENTS

| | | |
|---|---|---|
| 0095321 | 11/1983 | European Pat. Off. |
| 001432 | 1/1984 | European Pat. Off. |
| 161544 | 4/1985 | European Pat. Off. |
| 0151510 | 8/1985 | European Pat. Off. |
| 0357243A3 | 3/1990 | European Pat. Off. |
| 3428319 | 2/1987 | Fed. Rep. of Germany |
| 1028930 | 5/1966 | United Kingdom |

Primary Examiner—Arthur C. Prescott
Attorney, Agent, or Firm—Keil & Weinkauf

[57] ABSTRACT

A process for preparing formic acid by thermal cleavage of quaternary ammonium formates of the general formula I

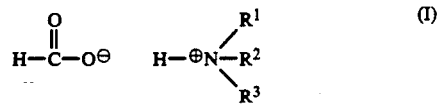

where
$R^1$, $R^2$ and $R^3$ are $C_1$- to $C_{14}$-alkyl, $C_3$- to $C_8$-cycloalkyl, aryl or $C_7$- to $C_{16}$-aralkyl, or together are 1,4- or 1,5-alkylene which is unsubstituted or substituted one to four times by $C_1$-to $C_4$-alkyl, with the proviso that the sum of the carbon atoms of $R^1$, $R^2$ and $R^3$ in the quaternary ammonium formates I is 7 to 40.

comprises carrying out the cleavage in the presence of secondary formamides of the general formula II

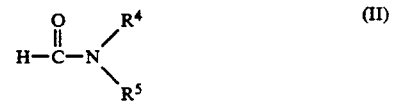

where
$R^4$ and $R^5$ are $C_2$- to $C_{10}$-alkyl, $C_3$- to $C_8$-cycloalkyl, aryl or $C_7$- to $C_{16}$-aralkyl, or together are 1,4- or 1,5-alkylene which is unsubstituted or substituted one to four times by $C_1$- to $C_4$-alkyl, which formamides boil 30° to 150° C. lower than the tertiary amine of the general formula III

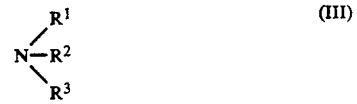

where $R^1$, $R^2$ and $R^3$ have the abovementioned meanings, contained in the formate I.

5 Claims, No Drawings

PREPARATION OF FORMIC ACID BY THERMAL CLEAVAGE OF QUATERNARY AMMONIUM FORMATES

The present invention relates to an improved process for preparing formic acid by thermal cleavage of quaternary ammonium formates in the presence of certain formamides.

EP-A-1,432 discloses that substituted N-alkyl-imidazoles facilitate the release, i.e. the separation, of formic acid from trialkyl formates. The high-boiling N-alkylimidazoles, however, are not sufficiently stable during continuous thermal loading in the presence of formic acid and require a high energy consumption during separation. In addition, the formic acid obtained in this way discolors on standing.

It is an object of the present invention to remedy the abovementioned disadvantages.

We have found that this object is achieved by a novel and improved process for preparing formic acid by thermal cleavage of quaternary ammonium formates of the general formula I

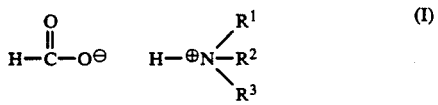

where
R$^1$, R$^2$ and R$^3$ are C$_1$- to C$_{14}$-alkyl, C$_3$- to C$_8$-cycloalkyl, aryl or C$_7$- to C$_{16}$-aralkyl, or together are 1,4- or 1,5-alkylene which is unsubstituted or substituted one to four times by C$_1$- to C$_4$-alkyl, with the proviso that the sum of the carbon atoms of R$^1$, R$^2$ and R$^3$ in the quaternary ammonium formates I is 7 to 40, which comprises carrying out the cleavage in the presence of secondary formamides of the general formula II

where
R$^4$ and R$^5$ are C$_2$- to C$_{10}$-alkyl, C$_3$- to C$_8$-cycloalkyl, aryl or C$_7$- to C$_{16}$-aralkyl, or together are 1,4- or 1,5-alkylene which is unsubstituted or substituted one to four times by C$_1$- to C$_4$-alkyl, which formamides boil 30° to 150° C. lower than the tertiary amine of the general formula III

where R$^1$, R$^2$ and R$^3$ have the abovementioned meanings, contained in the formate I.

The process according to the invention can be carried out as follows:

The quaternary ammonium formates I employed for the thermal cleavage (decomposition) can be obtained a) by direct reactions of the corresponding amines with formic acid according to GB-A-1,028,930 or U.S. Pat. No. 3,414,610 or b) by transition metal-catalyzed hydrogenation of carbon dioxide to formic acid in the presence of a nitrogen base such as described in EP-A-95,321, EP-A-151,510 or EP-A-357,243 or c) by reaction of methyl formate and water and subsequent extraction of the formic acid formed with a tertiary amine (DE-A-3,428,319) or with formamides as in U.S. Pat. No. 4,076,594, U.S. Pat. No. 4,262,140 or U.S. Pat. No. 4,326,073, or d) by reaction of methyl formate and water in the presence of imidazole derivatives (EP-A-1,432), formamides (EP-A-161,544) or with the tertiary amines III at from 50° to 200° C., preferably 100° to 150° C. particularly preferably 110° to 140° C., and at from 1 to 50 bar, preferably 1 to 20 bar, particularly preferably 5 to 15 bar.

Depending on the preparation process, the mixtures employed (crude mixtures) can contain further compounds such as, for example, solvents, unreacted reactants, coupling products formed and/or catalyst components in addition to the quaternary ammonium formate I. As a rule, for example according to process d), these crude mixtures contain as further compounds, for example, water, methanol and methyl formate, which can mainly be removed by distillation at normal pressure, in addition to the quaternary ammonium formate I.

The thermal cleavage according to the invention of the quaternary ammonium formates I can be carried out at from 0.01 to 2 bar, preferably 0.02 to 1 bar, particularly preferably 0.05 to 0.5 bar. The distillation temperature in this case depends mainly on the pressure.

The thermal cleavage is particularly convenient to carry out in distillation apparatus such as distillation columns, for example packed columns and bubble tray columns. Suitable packings are, for example, glass Raschig and Pall rings and, to avoid corrosion, preferably ceramic packings.

In the industrial practice of this novel process, a procedure is used in the case of methyl formate hydrolysis, for example, in which the hydrolysis is carried out in the presence of the base and water according to EP-A-1,432. After hydrolysis is complete, the substituted formamide is added and the mixture is worked up by distillation (removal of the residual methyl formate and water and the methanol formed). The anhydrous or largely anhydrous formic acid is then removed at the top in pure form in a distillation bulb under reduced pressure (advantageously up to about 150 mm Hg). The formamide added can then be removed from the free base, if desired, by distillation. However, the mixture of base and formamide remaining in the bottom can be recycled to the hydrolysis of the methyl formate without separation.

Other embodiments of the process are also possible. For instance, the hydrolysis of the methyl formate can also be carried out first without any addition. To complete the reaction, the formamide can be added first and then the base, or both can be added simultaneously.

The process is carried out particularly advantageously under continuous process control. In this case, methyl formate, methanol and water are removed at the top from the mixture discharged from the hydrolysis reaction, which consists of small amounts of methyl formate and water as well as methanol, formic acid and the base, by distillation at atmospheric pressure. The bottom extract from the first column is added to a second column, which is under vacuum (50–150 mm Hg). For easier removal of the formic acid, this second column contains the substituted formamide according to the invention.

This formamide is preferably selected so that it is found only on the lower separating stages of this column. This measure ensures that this formamide is largely kept away from the bottom and the virtually formamide-free base can be drawn off from the bottom and recycled to the hydrolysis step.

At the top, the anhydrous or largely anhydrous formic acid is taken off in pure form.

It is crucial to the success of the process that the formamide added has a higher volatility than the nitrogen base. From the large number of possible formamides, that selected preferably has a boiling point which is lower by 30° to 150° C., preferably 50° to 120° C., compared to the nitrogen base.

A further advantage of the addition of substituted formamides during the thermal separation is that tert-alkylamines with relatively low molecular weights can be employed for this purpose.

The substitutents $R^1$, $R^2$ and $R^3$ in the compounds I and III and $R^4$ and $R^5$ in the compounds II have the following meanings:

$R^1$, $R^2$, $R^3$, $R^4$ and $R^5$ are $C_3$- to $C_8$-cycloalkyl, such as cyclopropyl, cyclobutyl, cyclopentyl, cyclohexyl, cycloheptyl and cyclooctyl, preferably cyclopentyl, cyclohexyl and cyclooctyl, aryl such as phenyl, 1-naphthyl, 2-naphthyl, 1-anthryl, 2-anthyl and 9-anthryl, preferably phenyl, 1-naphthyl and 2-naphthyl, particularly preferably phenyl, $C_7$- to $C_{16}$-aralkyl, preferably $C_7$- to $C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, or $R^1$ and $R^2$ or $R^1$ and $R^3$ or $R^2$ and $R^3$ together are 1,4- or 1,5-alkylene which is unsubstituted or substituted by $C_1$- to $C_4$-alkyl one to four times, with the proviso that the sum of the carbon atoms of $R^1$, $R^2$ and $R^3$ in the compounds I and III is 7 to 40, preferably 1,4- or 1,5-alkylene which is unsubstituted or substituted by $C_1$- to $C_4$-alkyl one to four times, with the proviso that the sum of the carbon atoms of $R^1$, $R^2$ and $R^3$ in the compounds I and III is 10 to 24, such as —(CH$_2$)$_4$—, —(CH$_2$)$_5$—, —CH(CH$_3$)—CH$_2$—CH$_2$—, —CH$_2$—CH(CH$_3$)—CH$_2$—, ...

$R^1$, $R^2$ and $R^3$ are $C_1$- to $C_{14}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl and isododecyl, preferably $C_1$- to $C_8$-alkyl such as methyl, ethyl n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isohepty, n-octyl, isooctyl, particularly preferably $C_1$- to $C_4$-alkyl such as methyl, ethyl n-propyl, isopropyl, n-butyl, isobutyl, sec-butyl and tert-butyl, with the proviso that the sum of the carbon atoms of $R^1$, $R^2$ and $R^3$ is 7 to 40, preferably 10 to 24, $R^4$ and $R^5$ are $C_2$- to $C_{10}$-alkyl such as ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isoctyl, n-nonyl, isononyl, n-decyl, isodecyl, n-undecyl, isoundecyl, n-dodecyl and isododecyl, preferably $C_2$- to $C_8$-alkyl such as ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, particularly preferably $C_2$- to $C_4$-alkyl such as ethyl, n-propyl, isopropyl, n-butyl, isobutyl, sec-butyl and tert-butyl.

Suitable N-tert-alkylamines are in particular N-tripentyl-, N-trihexyl-, N-triheptyl- or N-trioctylamine, dimethyltetradecylamine, diethyltetrahexyl-, dimethyloctyl- or diethyloctylamine or else N,N'-dimorpholinoethane or N-hexylmorpholine.

EXAMPLES

Examples 1 to 4

Hydrolysis of Methyl Formate Using Tertiary Amines

The methyl formate conversion was determined in a 0.3 l stirred autoclave as a function of the type of base at a molar ratio of methyl formate:water:base = 1:1:1 and 120° C./with a residence time of one hour.

| Base | Conversion [%] |
| --- | --- |
| Dimethyltetradecylamine | 68 |
| Tri-n-octylamine | 68 |
| Dimethylcyclohexylamine | 78 |
| Tetramethylethylenediamine | 74 |

Examples 5 to 8

Recovery of Formic Acid by Distillation

In a continuous distillation apparatus, consisting of a bubble tray column (column I) (20 theoretical plates, diameter: 5 cm) and a packed column (column II) (5 mm glass Raschig rings, height 130 cm, diameter 4 cm), various hydrolysates, consisting of methyl formate, methanol, water, formic acid and base were separated into their components using the open procedure with respect to methyl formate, methanol and formic acid (water) and the closed procedure with respect to the base.

Comparative Example A

The mixture of 1025 g/h of tri-n-octylamine, 203 g/h of formic acid, 136 g/h of methanol, 100 g/h of methyl formate and 40 g/h of water leaving the hydrolysis reactor at 130° C. and 8 bar is added to the column I (bubble tray column) on the 15th theoretical plate (counted from the top). Rectification is carried out at atmospheric pressure and a bottom temperature of 158° C. The head temperature is 55° C. and the reflux ratio is 4:1. The anhydrous and formic acid-free head product of 129 g/h of methanol and 95 g/h of methyl formate is removed. The bottom is added to the center of the packed column I (diameter 4 cm, height 130 cm, 5 mm glass Raschig rings), which is operated under reduced pressure at 100 mbar. The thermal cleavage of the ammonium formate is carried out at a bottom temperature of 178° C. At a reflux ratio of R=4, a head product of 150 g/g of formic acid and 31 g/h of water is removed hourly at a head temperature of 47° C. The bottom product of the column II, which consists of 1024 g/h of tri-n-octylamine and 12 g/h of formic acid, is recycled to the hydrolysis reactor.

The formic acid contains about 2361 ppm of organic impurities. The formic acid losses are 20%.

Comparative Example B

The process is carried out with dimethyltetradecylamine instead of tri-n-octylamine in a manner similar to that in Example 5 and using the starting amount ratios and conditions indicated in Tables 1 and 2. The formic acid losses are about 24%, the formic acid obtained containing about 122 ppm of organic impurities.

Example 5

When carrying out the process as described in Comparative Example A, but adding dibutylformamide, several advantages are clear (see Tables 1 and 2). Under comparable conditions, the formic acid losses were only about 0.5% and the formic acid concentration obtained was 88%. Only 72 ppm of organic impurities were found in the formic acid.

Example 6

As described in Example 5, only using dimethyltetradecylamine and dibutylformamide as nitrogen bases. Under similar experimental conditions (see Tables 1 and 2), the formic acid losses were 9% and the formic acid concentration obtained was 91.5%. Only 4 ppm of organic impurities were found compared with 122 ppm in Comparative Example B.

These examples illustrate the hitherto unknown effect of the formamides which is crucial for the cleavage of the ammonium formates. Only the presence of these intermediate-boiling components makes possible the loss-free recovery of highly pure formic acid from ammonium formates. In contrast to the process described in DE-A-3,428,319, in which the removal of formic acid from ammonium formates is made possible by addition of hydrocarbons which form heteroazeotropes with water and formic acid, the formamide in this novel process does not have to be evaporated and can be kept in the column as an intermediate-boiling component. Depending on the formamide used, the inlet to the column 2 is therefore chosen to be above the separation section of the column.

Continuous Distillation of the Hydrolysates

TABLE 1

| | | | Distillation conditions | | | |
|---|---|---|---|---|---|---|
| Example | Base | RF | Column 1 Bottom [°C.] | [Atmospheric pressure] Head [°C.] | Column 2 Bottom [°C.] | [100 mbar] Head [°C.] |
| A | TOA | [4:1] | 158 | 55 | 178 | 47 |
| 5 | TOA/DBF | [4:1] | 150 | 58 | 180 | 48 |
| B | DMC1 4N | [4:1] | 148 | 55 | 181 | 52 |
| 6 | DMC1 4N/DBF | [4:1] | 150 | 65 | 180 | 47 |

RF = Reflux ratio; TOA = tri-n-octylamine; DBF = Dibutylformamide, DMC1 4N = Dimethyltetradecylamine

TABLE 2

| | Feed K 1 [g/h] | | | Distillate K 1 [g/h] | | | | Distillate K 2 [g/h] | | | Bottom K 2 [g/h] | | |
|---|---|---|---|---|---|---|---|---|---|---|---|---|---|
| | | Formic | | | Methyl | | Feed K 2 | | Formic | | | Formic | |
| Ex. | Total | acid | Amine/DBF | Total | formate | MeOH | [g/h] | Total | acid | H$_2$O | Total | acid | Amine |
| A | 1472 | 203 | 1025.2 | 222.4 | 95.3 | 118.9 | 1249.6 | 176 | 150 | 31 | 1036 | 12 | 1024 |
| 5 | 891.81 | 116.4 | 575.9/64 | 137.2 | 57.8 | 76.8 | 754.6 | 127 | 112 | 15 | 626 | 4.2 | 622 |
| B | 1411.1 | 229.6 | 928 | 246.9 | 129.9 | 103.12 | 1164.2 | 169.1 | 152 | 16.6 | 959 | 19 | 928 |
| 6 | 974.5 | 164 | 572.67/63.67 | 217.2 | 93.8 | 93.8 | 757.3 | 150.6 | 135 | 15 | 575.2 | 9 | 566 |

TABLE 3

| | | | | Continuous distillation of the hydrolysates (composition) | | | | |
|---|---|---|---|---|---|---|---|---|
| | | | | Distillate - Column 2 | | | Bottom - Column 2 | Losses |
| Ex. | Base [1:0.25 mol/mol] | Feed [ml/h] | Feed of formic acid Concentration [% by wt.] | Formic acid [%] | H$_2$O [%] | Org. impurities [ppm] | Formic acid [%] | Formic acid [%] |
| A | TOA | 2000 | 83.5 | 83.2 | 16.8 | 2361 | 1.1 | 20.5 |
| 5 | TOA/DBF | 1250 | 88.9 | 88.1 | 11.9 | 72 | 0.7 | 0.5 |
| B | DMC1 4N | 2000 | 86.3 | 89.9 | 10 | 122 | 2.4 | 24.2 |
| 6 | DMC1 4N/DBF | 1250 | 85.9 | 91.5 | 9.5 | 4 | 1.5 | 9.4 |

TOA = Tri-n-octylamine
DMC1 4N = Dimethyltetradecylamine
DBF = Dibutylformamide
H$_2$O = Water

We claim:

1. A process for preparing formic acid by thermal cleavage of quaternary ammonium formates of the general formula I

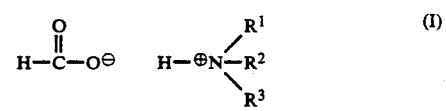

where $R^1$, $R^2$ and $R^3$ are $C_1$- to $C_{14}$-alkyl, $C_3$- to $C_8$-cycloalkyl, aryl or $C_7$- to $C_{16}$-aralkyl, or together are 1,4- or 1,5-alkylene which is unsubstituted or substituted one to four times by $C_1$- to $C_4$-alkyl, with the proviso that the sum of the carbon atoms of $R^1$, $R^2$ and $R^3$ in the quaternary ammonium formates I is 7 to 40, which comprises carrying out the cleavage in the presence of secondary formamides of the general formula II

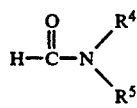
(II)

where $R^4$ and $R^5$ are $C_2$- to $C_{10}$-alkyl, $C_3$- to $C_8$-cycloalkyl, aryl or $C_7$- to $C_{16}$-aralkyl, or together are 1,4- or 1,5-alkylene which is unsubstituted or substituted one to four times by $C_1$- to $C_4$-alkyl, which formamides boil 30° to 150° C. lower than the tertiary amine of the general formula III $$\begin{array}{c} R^1 \\ N-R^2 \\ R^3 \end{array} \quad (III)$$

where $R^1$, $R^2$ and $R^3$ have the abovementioned meanings, contained in the formate I.

2. The process for preparing formic acid by thermal cleavage of quaternary ammonium formates I as claimed in claim 1, wherein the sum of the carbon atoms of $R^1$, $R^2$ and $R^3$ in the quaternary ammonium formates I is 10 to 24.

3. The process for preparing formic acid by thermal cleavage of quaternary ammonium formates I as claimed in claim 1, wherein N-dibutylformamide is used as the secondary formamide II.

4. The process for preparing formic acid by thermal cleavage of quaternary ammonium formates I as claimed in claim 1, wherein quaternary ammonium formates I of the tertiary amines III trihexylamine, triheptylamine, trioctylamine, dimethyltetradecylamine, N-hexylmorpholine or N,N'-dimorpholinoethane are used.

5. The process for preparing formic acid by thermal cleavage of quaternary ammonium formates I as claimed in claim 1, wherein the cleavage is carried out with secondary formamides II which boil 50° to 120° C. lower than the tertiary amine III contained in the formate I.

* * * * *